US00PP23083P2

(12) United States Plant Patent
Pierce

(10) Patent No.: US PP23,083 P2
(45) Date of Patent: Sep. 25, 2012

(54) ***CALIBRACHOA* PLANT NAMED 'CBRZ0002'**

(50) Latin Name: *Calibrachoa hybrida*
Varietal Denomination: CBRZ0002

(75) Inventor: Robert O. Pierce, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/134,404

(22) Filed: Jun. 7, 2011

(51) Int. Cl.
*A01H 5/00* (2006.01)

(52) U.S. Cl. ..... Plt./413

(58) Field of Classification Search ..... Plt./413
See application file for complete search history.

*Primary Examiner* — Annette Para
(74) *Attorney, Agent, or Firm* — Joshua L. Price

(57) ABSTRACT

A new *Calibrachoa* plant named 'CBRZ0002' particularly distinguished by the medium sized white and red-purple star-patterned flowers, deep green foliage, well-branched and mounding plant habit that is free-flowering, and with good vigor.

1 Drawing Sheet

Latin name of the genus and species of the plant claimed: *Calibrachoa hybrida.*

Varietal denomination: 'CBRZ0002'.

BACKGROUND OF THE NEW PLANT

The present invention comprises a new *Calibrachoa*, botanically known as *Calibrachoa hybrida*, and hereinafter referred to by the variety name 'CBRZ0002'.

'CBRZ0002' is a product of a planned breeding program. The new cultivar has medium sized white and red-purple star-patterned flowers, deep green foliage, well-branched and mounding plant habit that is free-flowering, and with good vigor.

'CBRZ0002' originated from a hybridization made in June 2006 in a controlled breeding environment in Gilroy, Calif. The female parent was an unpatented, proprietary plant designated '1609-2', with solid pink flowers, lighter green foliage and is later to flower.

The male parent of 'CBRZ0002' was also an unpatented, proprietary plant designated '1626-1', with rose flowers, wider diameter foliage, and longer internodes. The resultant seed was sown in June 2007.

'CBRZ0002' was selected as one flowering plant within the progeny of the stated cross in September 2007 in a controlled environment in Gilroy, Calif.

The first act of asexual reproduction of 'CBRZ0002' was accomplished when vegetative cuttings were propagated from the initial selection in September 2007 in a controlled environment in Gilroy, Calif.

BRIEF SUMMARY OF INVENTION

Horticultural examination of plants grown from cuttings of the plant initiated in September 2007, and continuing thereafter, has demonstrated that the combination of characteristics as herein disclosed for 'CBRZ0002' are firmly fixed and are retained through successive generations of asexual reproduction.

'CBRZ0002' has not been observed under all possible environmental conditions. The phenotype may vary significantly with variations in environment such as temperature, light intensity and day length.

Plant Breeder's Rights for this cultivar were applied for in Canada on Dec. 17, 2010 (10-7123) and in CVPO on Oct. 20, 2010 (2010/2235). 'CBRZ0002' has not been made publicly available more than -one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'CBRZ0002' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken from plants growing in a greenhouse trial in Gilroy, Calif. These plants were growing in 4.5 inch pots. The photographs were taken in early April 2011 and the plants were approximately four months of age. The descriptions and measurements in were taken in late April 2011 and the plants were then approximately four and a half months of age.

Color references are made to The Royal Horticultural Society Colour Chart (R.H.S.) 2001.

TABLE 1

DIFFERENCES BETWEEN THE NEW VARIETY 'CBRZ0002' AND A SIMILAR VARIETY

| | 'CBRZ0002' | 'Cal Paicoras' (U.S. Plant Pat. No. 19,256) |
|---|---|---|
| Flower size: | Larger | Smaller |
| Plant habit height: | Relatively more prostrate | Relatively taller |
| Branching habit: | More highly branched | Fewer branching |

Plant:

*Form, growth and habit*.—Compact and mounding habit, well-branched, pinching enhances the quantity of branches.

*Plant height*.—5.0-7.0 cm.

*Plant height* (*inflorescence included*).—Approximately 8.0-10.0 cm.

*Plant width*.—Approximately 40.0 cm.

Roots:

*Number of days to initiate roots and produce a rooted cutting*.—25-28 days at about 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 137B. Lower surface: Closest to RHS 137C.

*Mature, leaf color, upper surface*.—RHS 137A. Lower surface: Closest to RHS 137C.

*Length*.—3.0-3.3 cm.

*Width*.—0.7-0.8 cm.

*Shape*.—Narrowly elliptical.

*Base shape*.—Acuminate.

*Apex shape*.—Obtuse.

*Margin*.—Entire.

*Texture, upper surface*.—Pubescent mainly on the margins. Lower surface: Pubescent mainly on the margins.

*Color of veins, upper surface*.—Between RHS 144B and RHS 144C.

*Color of veins, lower surface*.—Between RHS 144B and RHS 144C.

*Petiole color*.—Between RHS 144B and RHS 144C.

*Length*.—0.1-0.2 cm.

*Diameter*.—0.1 cm.

*Texture*.—Pubescent.

Stem:

*Quantity of main branches per plant*.—About 10.

*Color of stem*.—Closest to RHS 143C, some have slight anthocyanin patches of lighter but greyer than RHS 177A.

*Length of stem*.—Approximately 23.0-26.0 cm.

*Diameter*.—0.2 cm at midpoint.

*Length of internodes*.—0.5-2.0 cm.

*Texture*.—Hirsute; some glandular hairs.

*Color of pedicel*.—Closest to RHS 146C.

*Length of pedicel*.—1.9-2.1 cm.

*Diameter of pedicel*.—0.1 cm.

*Texture of pedicel*.—Hirsute; few glandular hairs.

Inflorescence:

*Type*.—Flowers solitary in upper leaf axis; flowers face mainly horizontally, mostly 5 fused lobes forming a funnel form flower. Continuous flowering throughout the summer.

*Quantity of inflorescences per plant*.—Approximately 80-100 plus numerous buds.

*Lastingness of individual blooms on the plant*.—About 7-9 days.

*Fragrance*.—None.

Bud (just when opening/showing color):

*Color*.—RHS 1C to RHS 1D with RHS 27D at the apex, and RHS 165 midveins.

*Length*.—2.2-2.4 cm.

*Width*.—0.4-0.5 cm.

*Shape*.—Oblong.

Immature inflorescence:

*Flower horizontal diameter*.—2.2-2.7 cm.

*Color petals, upper surface*.—RHS 155D mainly showing at the margins; heavily overlaid RHS N74A at the center of petals, bleeding out to RHS N74B towards the margins; RHS 71A midvein and blush at throat.

*Color petals, lower surface*.—RHS 155D ground color; overlaid with light hues of RHS 65D and RHS 65C with RHS N79A midveins.

Mature inflorescence:

*Flower horizontal diameter*.—3.3-3.5 cm.

*Flower height* (*vertical*).—3.0 cm.

*Flower depth*.—2.2-2.5 cm.

*Color petals, upper surface*.—RHS N155B ground color, mainly showing at the margins and overlaid RHS N74B that matures to between RHS 72B and RHS N74C, with still a slight accent at the apex of RHS N74B; RHS N77B midveins that become lighter towards the margins.

*Color, petals, lower surface*.—RHS N155B ground color with hints of RHS 65D towards the apex, streaks of RHS 65A along the midvein; RHS N77A midvein.

*Apex shape*.—Rounded.

*Margin*.—Entire.

*Waviness of petals*.—None.

*Petal lobation*.—Moderate.

*Petal texture*.—Papillose.

*Petal texture* (*under*).—Pubescent along margins and midveins.

*Corolla tube color outside*.—Muted RHS 8B with RHS 174A veins and RHS 176B midveins. Inside: RHS 7A with RHS 174A midveins and veining.

*Corolla tube length*.—1.6-1.8 cm.

*Corolla texture, outside*.—Pubescent; glandular hairs. Inside: Papillose.

Sepals:

*Color, upper surface*.—RHS 143C with darker apex. Lower surface: RHS 143C with darker apex.

*Length*.—1.0-1.6 cm.

*Width*.—0.2 cm at base.

*Shape*.—Lanceolate.

*Apex shape*.—Acute.

*Based*.—Fused.

*Margins*.—Entire.

*Texture, upper surface*.—Glabrous; pubescent at margins. Lower surface: Pubescent.

Reproductive organs:

*Pistil*.—1.

*Length*.—1.1 cm.

*Style color*.—Closest to RHS N144D.

*Style length*.—0.7 cm.

*Stigma color*.—RHS N144C.

*Ovary color*.—RHS 150C.

*Stamens*.—5.

*Color of filaments*.—RHS 145C.
*Length filaments*.—0.8-1.0 cm.
*Anther color*.—RHS 7B.
*Anther length*.—Approximately 0.1 cm.
*Anther shape*.—Oval.
*Color of pollen*.—RHS 9B.
*Pollen amount*.—Moderate.
*Fertility/seed set*.—Has not been observed on this hybrid.

Disease/pest resistance: Disease/pest resistance has not been observed on this hybrid.

What is claimed is:

1. A new and distinct variety of *Calibrachoa* plant named 'CBRZ0002' substantially as illustrated and described herein.

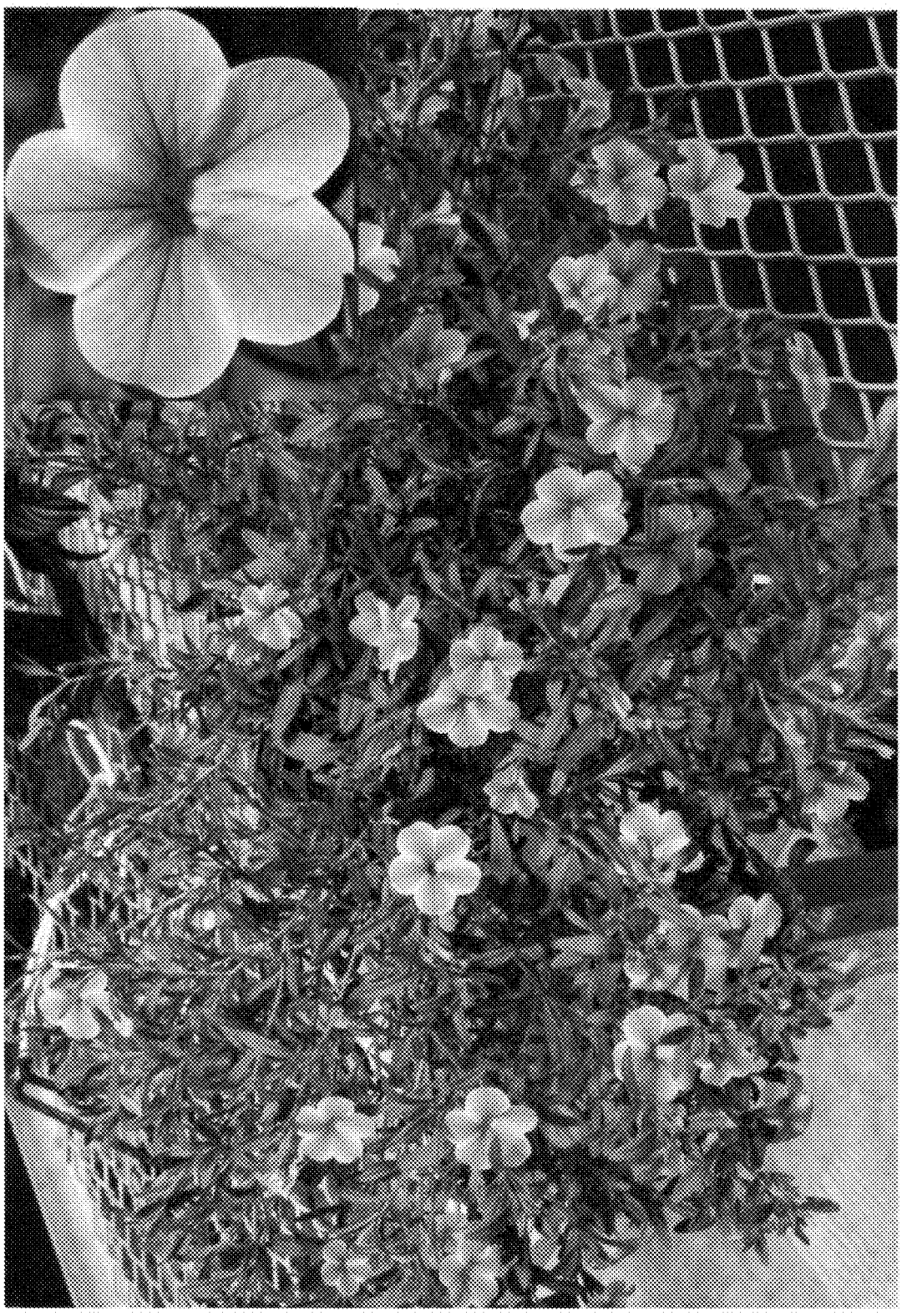

* * * * *